(12) United States Patent
Russo

(10) Patent No.: US 7,779,842 B1
(45) Date of Patent: Aug. 24, 2010

(54) SUCTION SYSTEM WITH HIGH EFFICIENCY SUCTION CONTROL VALVE

(76) Inventor: Ronald D. Russo, 8 Candleberry Rd., Barrington, RI (US) 02806

(*) Notice: Subject to any disclaimer, the term of this patent is extended or adjusted under 35 U.S.C. 154(b) by 1316 days.

(21) Appl. No.: 11/194,780

(22) Filed: Aug. 1, 2005

Related U.S. Application Data

(63) Continuation-in-part of application No. 10/058,540, filed on Jan. 28, 2002, now Pat. No. 6,923,184.

(60) Provisional application No. 60/266,200, filed on Feb. 5, 2001, provisional application No. 60/271,481, filed on Feb. 27, 2001, provisional application No. 60/305,774, filed on Jul. 17, 2001.

(51) Int. Cl.
  *A61M 16/00* (2006.01)
  *A61M 1/00* (2006.01)
  *A62B 9/06* (2006.01)

(52) U.S. Cl. ............... 128/207.14; 128/205.19; 604/119

(58) Field of Classification Search ............ 128/200.26, 128/205.12, 205.24, 205.16, 205.18, 207.14, 128/207.16, 205.19; 604/118, 119, 249, 604/250, 251, 163, 171; 251/214, 337, 321, 251/330; 137/381
See application file for complete search history.

(56) References Cited

U.S. PATENT DOCUMENTS

| 3,335,727 | A | * | 8/1967 | Spoto | 604/119 |
| 5,220,916 | A | * | 6/1993 | Russo | 128/207.16 |
| 5,354,267 | A | * | 10/1994 | Niermann et al. | 604/32 |
| 5,496,287 | A | * | 3/1996 | Jinotti | 604/249 |
| 5,664,564 | A | * | 9/1997 | Palmer | 128/205.19 |
| 5,676,136 | A | * | 10/1997 | Russo | 128/205.24 |
| 5,730,727 | A | * | 3/1998 | Russo | 604/118 |
| 5,775,325 | A | * | 7/1998 | Russo | 128/205.12 |
| 6,044,908 | A | * | 4/2000 | Wyatt | 166/332.4 |
| 6,070,582 | A | * | 6/2000 | Kee | 128/207.16 |
| 6,494,203 | B1 | * | 12/2002 | Palmer | 128/202.27 |
| 6,923,184 | B1 | * | 8/2005 | Russo | 128/207.14 |

* cited by examiner

*Primary Examiner*—Justine R Yu
*Assistant Examiner*—Kristen C Matter
(74) *Attorney, Agent, or Firm*—Robert J Doherty

(57) ABSTRACT

An improved high efficiency suction control valve providing unobstructed fluid flow in its activated suction applied mode for removal of viscous secretions at a low level of applied input suction through the catheter. The valve provides positive sealing between a hand-operated plunger and the valve passageway walls against which the plunger engages by slightly over sizing the plunger walls such that the plunger walls expand against a further suction passageway. Similar sealing is provided between the plunger and passageway above the suction passageway.

58 Claims, 12 Drawing Sheets

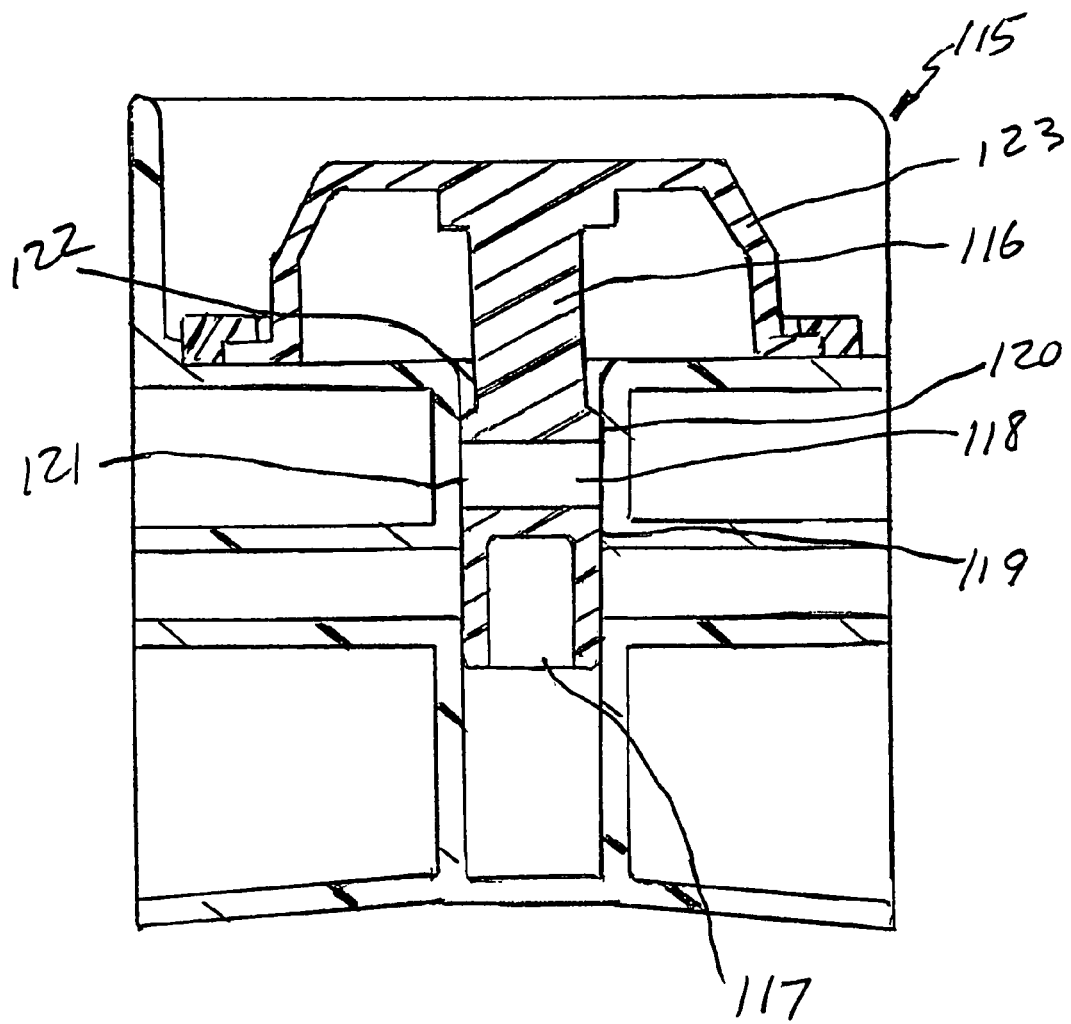

SUCTION SYSTEM WITH HIGH EFFICIENCY SUCTION CONTROL VALVE

RELATED APPLICATIONS

This application is a continuation-in-part of U.S. patent application Ser. No. 10/058,540 filed Jan. 28, 2002 now U.S. Pat. No. 6,923,184 issued Aug. 2, 2005.

The inventor claims the full benefit of the following U.S. Provisional Patent Applications: U.S. Patent Application No. 60/266,200 entitled TRANSVERSE CLOSED TRACHEAL SUCTION DEVICE filed Feb. 5, 2001; U.S. Patent Application No. 60/271,481 entitled COMPACT CLOSED TRACHEAL SUCTION DEVICE filed Feb. 27, 2001; and U.S. Patent Application No. 60/305,774 entitled HIGH EFFICIENCY SUCTION CONTROL VALVE filed Jul. 17, 2001.

BACKGROUND OF THE INVENTION

This invention relates to suction catheter systems with suction control valves and especially those used in medical applications. Suction catheters are used to remove secretions from a patient's airway and catheters fall into two categories of single use disposable: "open" style catheters and the newer type "closed" systems manufactured by Ballard Medical Inc. and SIMS Portex.

"Open" style catheters typically use a normally open suction control valve such as those described in U.S. Pat. No. 4,534,542 to Russo. The "closed" tracheal suction systems typically use a normally closed suction control valve as described in U.S. Pat. No. 4,569,344 to Palmer, U.S. Pat. No. 4,696,296 also to Palmer, and U.S. Pat. No. 5,073,164 to Hollister. The closed systems usually comprise a frontal connector attachable to a ventilator and the patient's endotracheal tube along with a protective sleeved suction catheter and a normally closed suction control valve. The valve must be normally closed to prevent the loss of administered ventilation when the patient is not being suctioned since the closed system is left attached to the patient and the breathing circuit at all times.

The normally closed valves described in the above patents to Palmer and Hollister are actually in commercial use as part of the Ballard Medical Trach-Care® product and the SIMS Portex Steri-Cath®, and they suffer from several limitations that impact their clinical efficacy and their low suction efficiency. As noted, the valves used in both the Ballard Medical and SIMS Portex devices are 100% obstructed when they are positioned in their non-activated, non-suction applied mode. However, they remain in a partially blocked or partially obstructed flow path position when they are activated in their suction applied mode. This means that suction levels have to be set exceedingly high in order to equal the suction efficiency of the open straight through flow paths of the open style catheters. Actual suction levels in an open to style catheter are usually set at a clinically documented low suction level of about 125 mm Hg and will efficiently remove viscous secretions with little mucosal tissue grab and trauma at that level.

By comparison, actual levels in some closed systems have to be set at 300 mm Hg to approach the suction efficiency of the open style devices. Even at that level, the closed devices sometimes have difficulty removing viscous secretions due to the obstructive, restrictive flow path design of their normally closed valves that also decreases airflow at the distal tip of the catheter. Also, since the Palmer/Ballard Medical valve type has a spring action biased sealing member acting on a valve seat, the seating surface is more prone to being clogged by viscous secretions especially if the valve is not flushed well after use. Clogging of the valve seat may leave the valve partially open such that the valve may have a slow leakage of ventilated gases since it may not seal 100% closed. In addition, the Palmer/Ballard Medical valve type has many cooperating parts requiring more expensive manufacturing in assembly time and labor.

Towards this end, a Suction System with High Efficiency Suction Control Valve has been conceived to provide a normally closed suction control valve which is non-obstructive to both fluid and airflow in its suction applied mode and will only require the low 125 mm Hg safe level of suction.

Further, closed tracheal suction devices such as the Ballard Trach-to Care® and SIMS Steri-Cath® are being used for repeated suctioning and secretion removal procedures, and these devices can stay connected to a patient's respiratory system for up to 72 hours or 3 days. Ballard Medical has recently commercially introduced a 72 hour product (Trach-Care 72) which is the commercial embodiment of U.S. Pat. No. 6,227,200 issued to Crump et al and assigned to Ballard Medical Products which references many of the prior art patents. However, this new Trach-Care® 72 still uses the same obstructive suction control valve used in the original Trach-Care®. Viscous secretions, which may tend to partially accumulate in the frontal connector portion of closed tracheal suction devices, can easily be re-introduced by the catheter during subsequent suctioning procedures, which may cause VAP (ventilator-associated pneumonia). Complete removal of secretions throughout the system is of paramount importance. It would be ideal to provide a high efficiency suction control valve that could be utilized as part of a closed tracheal suction system which completely isolates the catheter when not in use and which thoroughly and effectively cleans all secretions after use and also prevents the accumulation of secretions within the system especially within the connector. Thus, there is a need for a catheter apparatus that will solve all the aforementioned problems.

Other objects, features and advantages of the invention shall become apparent as the description thereof proceeds when considered in connection with the accompanying illustrative drawings.

SUMMARY OF THE INVENTION

The ideal normally closed suction control valve would produce a high suction efficiency at a low level of applied suction of about 125 mm Hg while not restricting airflow at the distal tip of the suction catheter. The present invention meets this objective for the first time in an inexpensive single patient use disposable medical device. The device of the present invention comprises only three injection-molded parts and is very inexpensive to produce and assemble. The device of the present invention has a rigid ABS or PVC plastic housing into which is inserted a synthetic molded rubber plunger which is to airtight hermetically sealed into place ultrasonically by a seal ring also made from rigid ABS or PVC plastic.

The plunger normally seals off the main suction passageway when in a non-suction applied mode. Upon manual depression of the plunger button actuator, the main central suction passageway is forced open by an upper suction cross lumen in the plunger. Manual release of the plunger automatically returns the valve to its normally closed position. The valve can be used as part of any catheter or suction tube device but is especially applicable for use in any closed tracheal suction system.

Ideally, however, the high efficiency valve is combined and made part of a closed tracheal suction system which prevents VAP by providing for isolation of the catheter when not in use, thorough cleansing of the catheter, effective removal of any catheter secretions withdrawn and accumulated secretions within the system after catheter retraction back into the system after suctioning a patient's respiratory system is completed, and the application of a safe, low level of suction at the catheter distal tip to reduce mucosal tissue damage during suctioning.

It is therefore an object of the present invention to meet all the above objects.

It is another object of the present invention to provide a 100% to normally closed airtight catheter isolator seal that can be opened or closed solely by advancing or retracting a catheter or tube through the seal.

It is another object of the present invention to provide a single catheter wiper as part of a catheter-cleaning chamber to thoroughly remove secretions from the outside of the catheter and to deposit those secretions in the catheter-cleaning chamber distal to the wiper.

It is a further objective to provide an airflow vortex action catheter-cleaning chamber that effectively removes accumulated secretions from the catheter-cleaning chamber and the ventilator connector.

It is a further objective to provide a single combination bronchial lavage and catheter rinse port that accesses the catheter-cleaning chamber.

It is a further objective to utilize the efficiency of the high efficiency suction control valve to remove tracheal secretions within the airway at a low level of input suction to prevent mucosal tissue damage.

It is a further objective to utilize the efficiency of the high efficiency suction control valve to clean the catheter prior to retraction into a catheter isolator tunnel.

In accordance with another aspect of the present invention, a replaceable catheter cartridge is provided such that the frontal connector that incorporates the catheter-cleaning chamber and isolator seal can remain to connected to the patient without losing ventilator gases or PEEP when the catheter cartridge is replaced.

DESCRIPTION OF THE DRAWINGS

In the drawings which illustrate the best mode presently contemplated for carrying out the present invention:

FIG. 15 is a cross-sectional side view of an alternate embodiment to of the plunger portion of the valve depicting lower and upper outwardly expanding sidewalls forming a sealing engagement when the valve is its normally sealed closed non-suction applied position.

DESCRIPTION OF THE INVENTION

Figure 1:
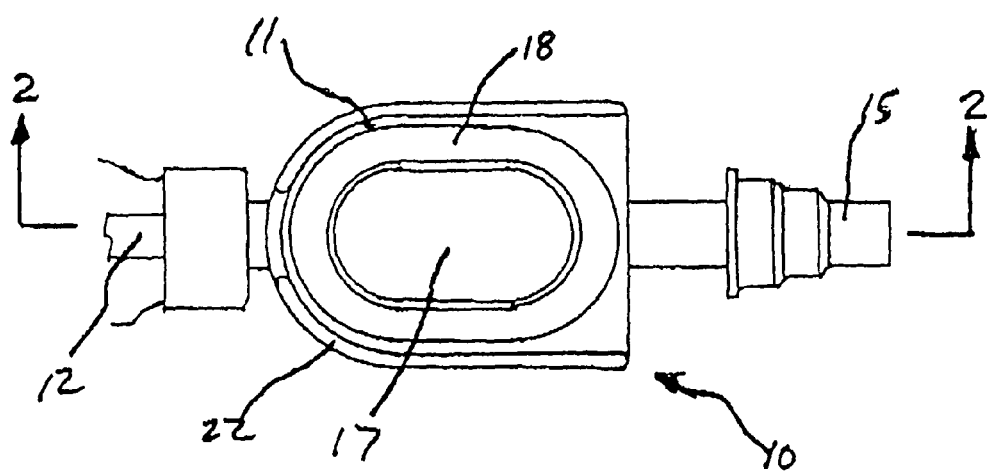
FIG. 1 is a top view of the high efficiency suction control valve.
Figure 2:
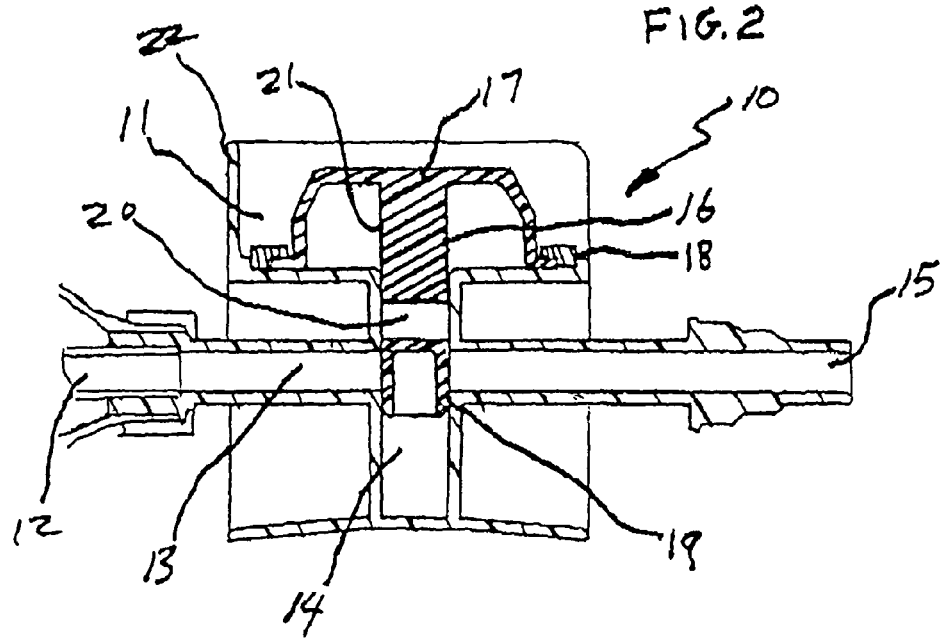
FIG. 2 is a side cross-sectional view thereof taken along lines 2-2 in FIG. 1 showing the device positioned in its normally closed non-suction applied mode.

FIGS. 1 and 2 clearly show the suction control valve 10 in its normally positioned closed non-suction applied mode. The valve 10 has a one-piece rigid injection molded housing 11 made from ABS or PVC plastic which can solvent cement to any catheter 12. The housing 11 has a main first central linear straight through fluid and airflow passageway 13 that is in straight-line communication with the catheter 12. The transversing passageway 13 is transverse to second passageway 14. The passageway 13 extends past the second passageway 14 rearward to built-in suction connector 15 which permits direct connection to any source of regulated vacuum or suction via suction tubing. Inserted into second transversing passageway 14 is synthetic rubber molded plunger 16 that is typically circular in cross section and also has a top resiliently manually depressively activated button actuator portion 17 that is generally oval in shape. A sealing ring 18 hermetically seals plunger 16 and actuator portion 17 in place. The seal ring 18, which is constructed from rigid molded ABS or PVC plastic, is ultrasonically sealed to the adjacent portions of the actuator portion 17 such that the plunger and actuator are completely sealed off from atmosphere. The plunger 16 has a lower piston 19 integrally formed therewith which not only blocks but hermetically seals off central linear passageway 13 in an airtight manner. The plunger 16 and piston 19 have slightly oversized sidewalls 21 which, when not restrained, resiliently expand outward to form a 100% leak proof airtight hermetic seal within central passageway 13 and further act to seal off any leakage of suction or secretions out the valve 10 even if the valve 10 is left attached to a source of vacuum or suction such as by leaving the valve connected to suction tubing. Partially encircling the periphery of the actuator portion 17 and part of the housing 11 is a built in guard flange 22 formed as part of the housing 11 which is slightly higher in height than the actuator portion 17. This guard flange 22 permits inadvertent depression or activation of actuator portion 17 if a patient were to roll over on top of valve 10. This guard flange 22 acts as a safety feature.

Figure 3:
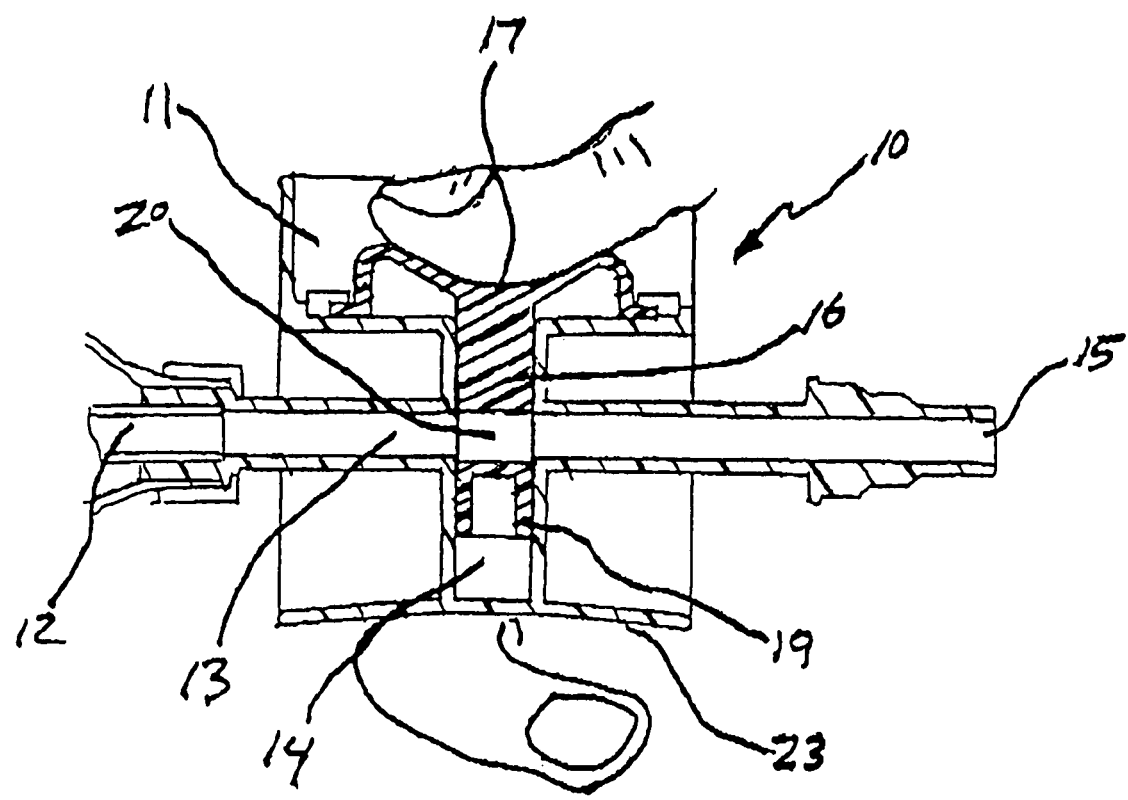
FIG. 3 is a side cross-sectional view of the high efficiency suction control valve showing the device positioned in its fully open suction applied mode.

FIG. 3 is a cross-sectional side view of valve 10 shown in its suction applied mode versus its non-suction applied mode depicted in FIG. 2. When manually depressed actuator portion 17 is resiliently deformed and flexed downward to slideably move plunger 16 and piston 19 downward within second passageway 14 such that cross lumen 20 aligns itself and fully and completely opens up central passageway 13, the unobstructed and unrestrictive fluid and airflow is permitted to take place through central passageway 13.

When vacuum or suction is applied by depressing actuator 17, aspirated secretions will flow through catheter 12, on through passageway 13, through cross lumen 20 in plunger 16 and out through connector 15 in an unobstructed unrestrictive manner from catheter 12 straight through valve 10 and out through the suction source. A clinically safe and desirable low 125 mm Hg suction applied level is all that is needed to move the most viscous of secretions through valve 10 since there is no obstruction to either fluid or airflow through the valve 10. The valve can also take full advantage of the suction input airflow rate that will substantially increase suction efficiency to its highest level.

The housing 11 is provided with a molded-in lower finger rest 23 as shown. A very slight amount of silicone stopcock grease can be applied to plunger 16 prior to assembly into transverse second passageway 14 to act as an anti-friction lubricant for smooth up and down slideable action of the plunger 16 and piston 19 in passageway 14.

Manual release of actuator portion 17 will automatically return plunger 16 to its original normally closed, sealed, non-suction applied mode position as shown in FIG. 2.

In use, actuator portion 17 can be depressed either continuously or intermittently when suction needs to be applied. Also, the actuator portion 17 is shown in an oval configuration such that the insertion of plunger 16 into transverse passageway 14 will automatically orient the cross lumen 20 in its proper aligned relationship with second transverse passageway 14 and central passageway 13 providing a straight through linear internal smooth laminar flow path unlike the prior art devices which have distorted tortuous disruptive flow paths that impede, obstruct, and restrict the flow of viscous secretions to cause the secretions to block and build up.

In essence, the oval shape automatically positions the plunger 16 into its proper alignment with respect to passageways 13 and 14 such that the valve can only be assembled in manufacturing in its correct foolproof manner. In summary, the valve 10 provides all the efficiencies and advantages of an open style valve only in a normally closed valve made from three simple injection molded components that can be rapidly manufactured and assembled into a to finished suction control valve at low cost. Unlike the obstructive spool valves of Palmer and Hollister as well as all the other known prior art valves, the present valve invention provides the highest degree of suction efficiency in a normally closed suction control valve as part of a suction system. Although an oval button actuator and round plungers are shown, many other configurations such as square plungers and rectangular actuators could be designed and used without departing from the broad scope of this underlying suction control valve invention.

Figure 4:
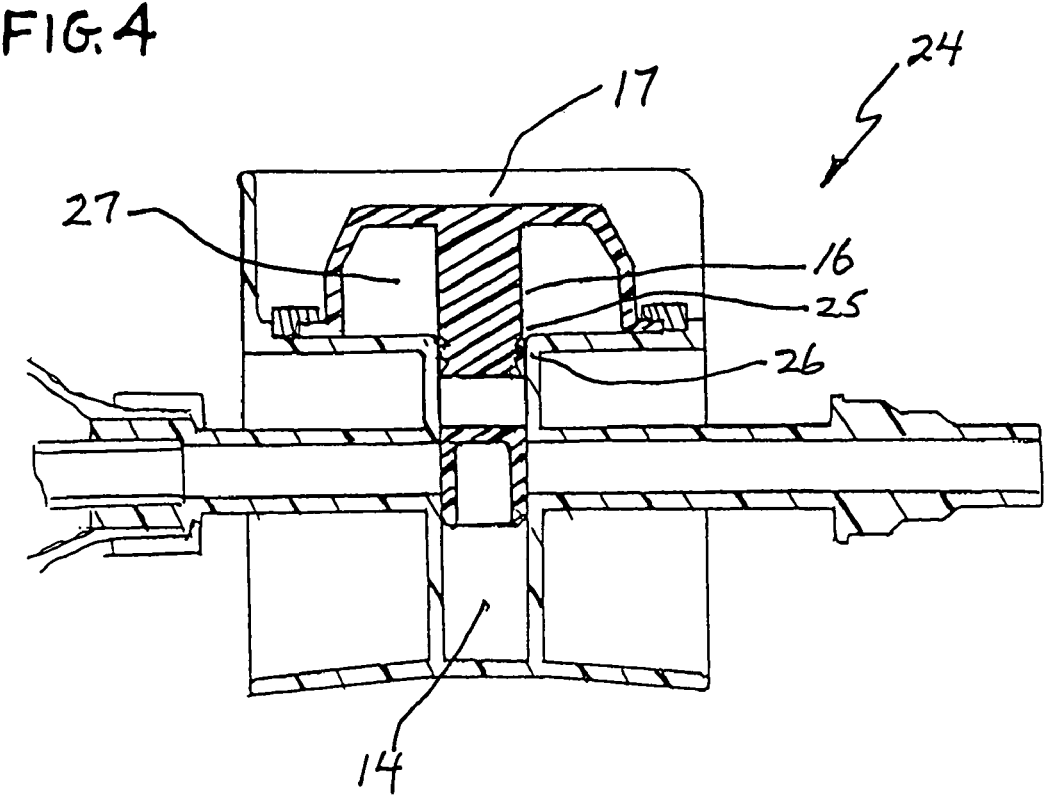
FIG. 4 is a side cross-sectional view of an alternate embodiment of the high efficiency suction control valve showing a molded-in "O" ring wiper seal as part of the upper plunger.

FIG. 4 shows an alternate embodiment 24 essentially identical to the suction control valve 10 depicted in FIG. 2 with the exception that the plunger 16 has an upper stem portion 25 incorporating a built-in molded wiper seal "O" ring 26 as part of the plunger 16 which acts to prevent any secretions from entering in chamber 27 under button actuator 17.

Figure 5:
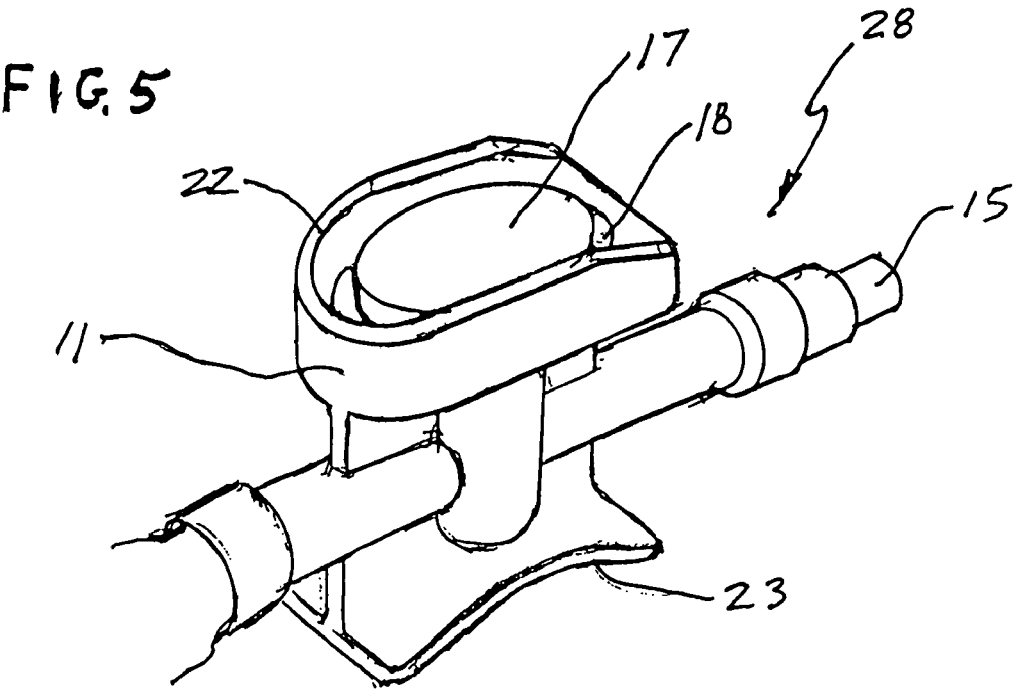
FIG. 5 is a perspective view of the high efficiency suction control valve.

FIG. 5 shows a clear perspective view of the valve depicted in FIG. 2 with all the main externally visible portions identified.

Figure 6:
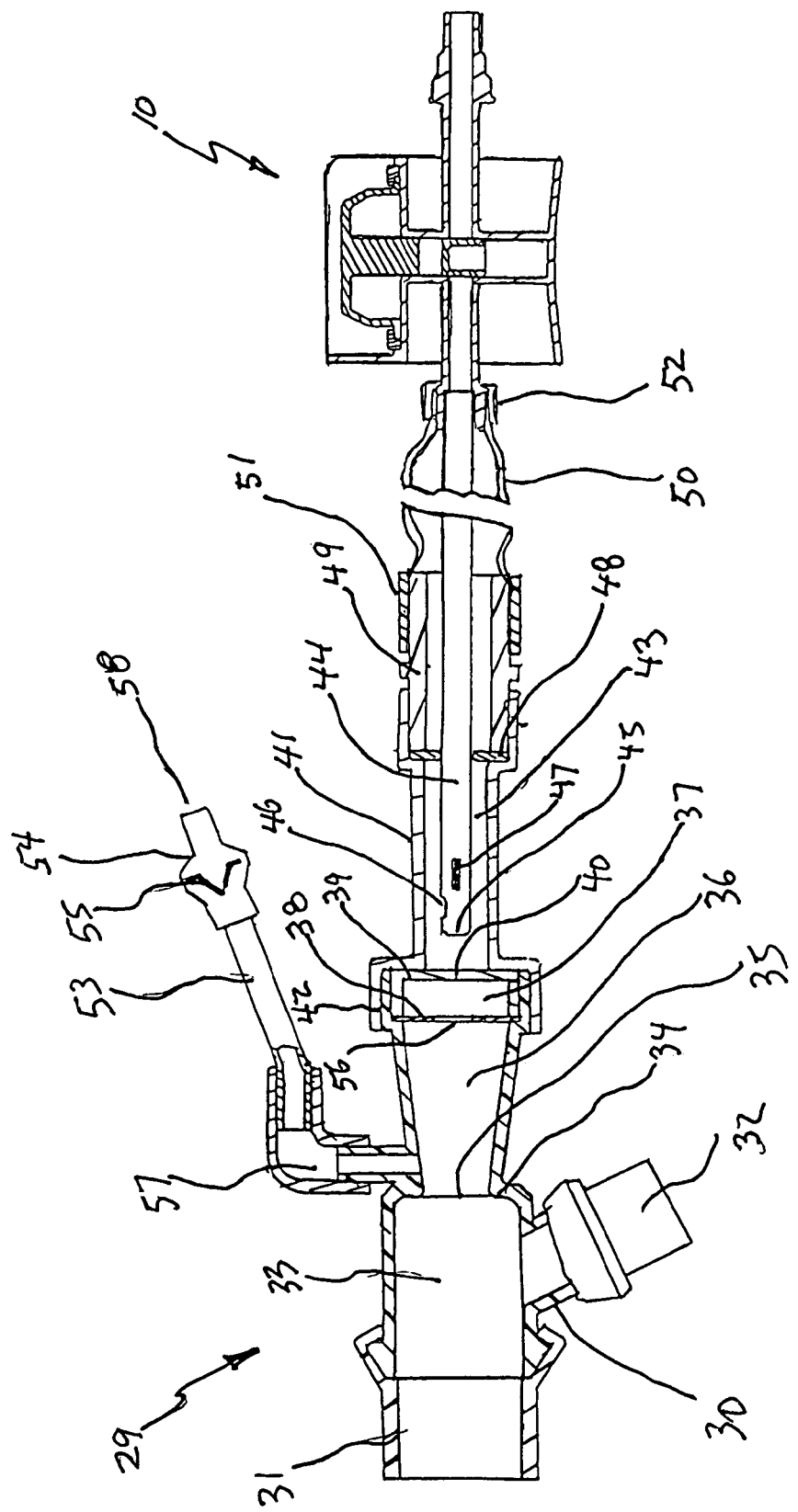
FIG. 6 is a side cross-sectional view of a complete closed tracheal suction system that uses the high efficiency suction control valve.

FIG. 6 clearly depicts the closed tracheal suction system 29 of the present invention incorporating valve 10 as part of its assembly and comprises a frontal connector 30 with a frontal swivel 31 that directly attaches to a patient tracheal tube and a side swivel 32 for connection to the ventilator circuit for the delivery of ventilator gases into inner air passage 33 which in turn delivers gases through front swivel 31 into the patient's tracheal tube and respiratory system. Rearward of passage 33 is wall 34 having a somewhat narrowed entrance opening 35 which opens up into a larger funnel-shaped catheter-cleaning chamber 36. Located just behind narrowed opening 35 is a single combination lavage/flush access port 57 that is solvent bonded onto chamber 36. All the elements formed as part of connector 30 are injection molded of clear rigid ABS or PVC plastic. Further rearward of chamber 36 is collar recess 37. The passage 33, chamber 36 and collar recess 37 are formed as one unitized clear or transparent plastic piece. Fitted into recess 37 is thin walled silicone catheter wiper 38 having an undersized wiper circular hole 56 dimensioned to give the wiper contact fit with differently sized catheters from 10 fr up to 18 fr in outside diameter. Slightly downstream of wiper 38 is isolator silicone molded diaphragm isolator seal 39 having a centrally located through slit 40. It is also contemplated that wiper 38 and isolator seal 39 can be formed as one unitized silicone molded part and not as separate components.

The seal 39 is slightly press fit into recess 37 such that slit 40 is normally biased sealed shut preventing the escape of any administered pressurized gasses to atmosphere. The injection molded tubular housing 41 has a collar 42 which is solvent cemented to recess 37 effectively joining the housing 41 to connector 30 and sealing in isolator seal 39. The housing 41 has an interior catheter isolator tunnel 43 which houses PVC suction catheter 44 with distal tip opening 45 having a side vent hole 46 and black catheter indicator mark 47. The silicone catheter tunnel seal 48 is held in place by a solvent-bonded fitting 49. The catheter 44 is usually about 22 inches long and is protectively surrounded by a thin collapsible polyethylene sleeve 50 which is captured onto fitting 49 by press fit ring 51 and attached to the valve 10 by rear ring 52. It should be noted that the tubular housing 41 is opaque such that once the catheter 44 is retracted back into isolator tunnel 43 both the tubular housing 41 and the black indicator mark 47 are not visible. Also, port 57 has short tubing 53 that terminates in molded housing 54 which encases a one-way silicone molded duckbill anti-reflux valve 55. The housing 54 has a luer opening 58 attachable to any fluid vial or syringe. As can be seen, system 29 is formed in one complete unitized system utilizing high efficiency valve 10.

Figure 7:
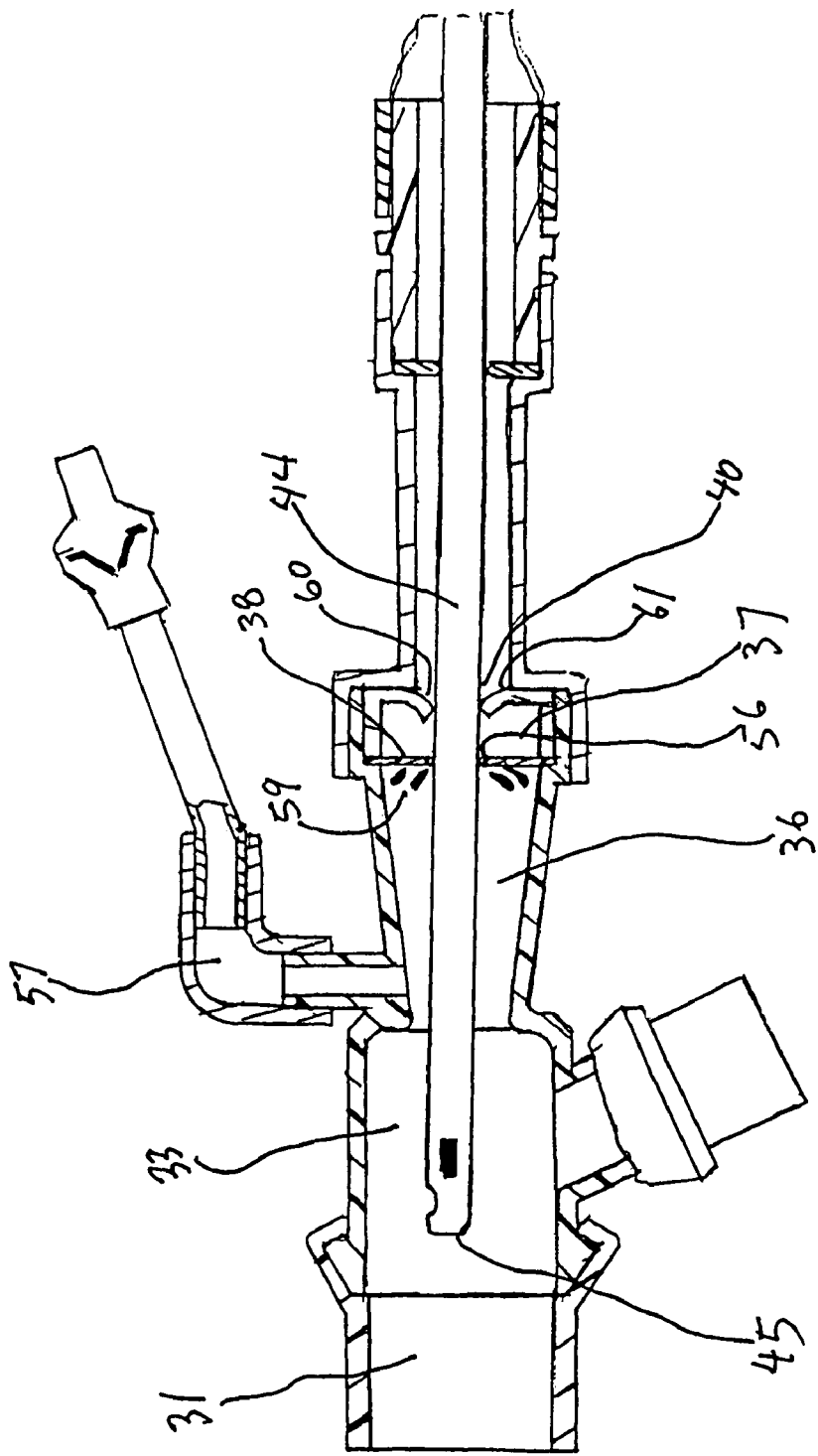
FIG. 7 is an enlarged partial side cross-sectional view of the closed tracheal suction system of FIG. 6 showing the suction catheter being withdrawn in the vortex catheter-cleaning chamber.

As can be seen in FIG. 7, the catheter 44 can be slideably manually advanced and retracted and will solely by itself without any external force acting upon isolator seal 39 open and close slit 40 on isolator seal 39. The catheter 44, once advanced from isolator tunnel 43, will cause slit 40 to open forming resilient flexible leafs 60 and 61 that will purse open and sealably close in an airtight fashion in response to advancement or retraction of the catheter 44 through isolator seal 39. The catheter 44 can be fully advanced through front swivel 31 into a patient's airway. Once fully advanced into the airway, suction is either intermittently or continuously applied upon actuation of suction valve 10 as the catheter 44 is being withdrawn back from the airway and back into the passage 33. Secretions 59 will be wiped from the outside of catheter 44 by catheter wiper 38 as the catheter is being fully withdrawn. Since the suction valve 10 is highly efficient at secretion removal within the airway, secretions remaining on the outside of the catheter 44 will be minimal compared to the obstructed suction control valves of the prior art. However, some will accumulate as secretions 59 in front of wiper 38.

Figure 8:
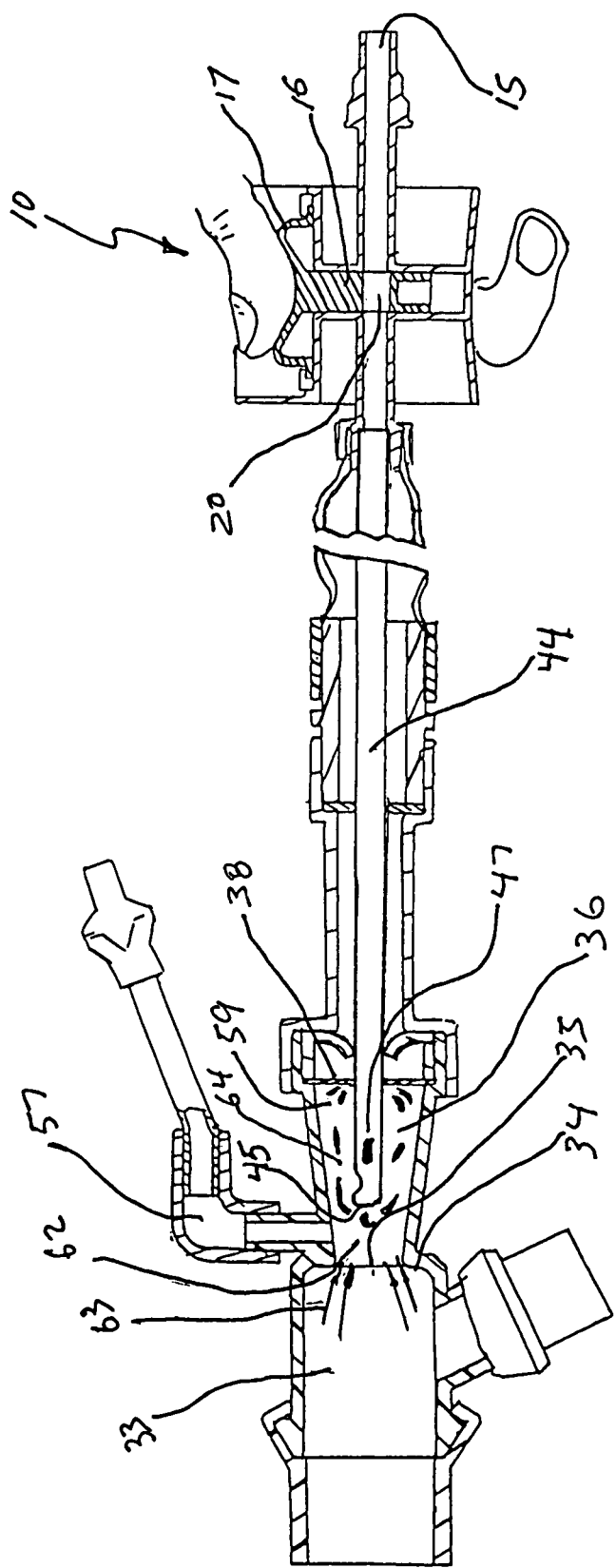
FIG. 8 is a side cross sectional view of the closed tracheal suction system of FIG. 6 showing the vortex action of the catheter-cleaning chamber when the catheter is being withdrawn and suction is applied to the distal tip of the catheter by the high efficiency suction control valve.

FIG. 8 depicts the catheter 44 being retracted back into the catheter-cleaning chamber 36 after suctioning such that the black indicator mark 47 clearly shows catheter tip 45 located within chamber 36.

Since the chamber 36 is progressively funnel shaped, applied suction will provide two actions leading to removal of accumulated secretions 59 from wiper 38. The first action creates a low pressure lift zone 62 at narrow opening 35 that will tend to lift secretions 59 off wiper 38. This low-pressure zone 62 is created as air 63 rushes pass narrow opening 35 that will also suck back any secretions left in the connector passage 33 in chamber 36. The second action creates a swirling vortex action 64 within cleaning chamber 36 to effectively lift off and remove secretions 59 from wiper 38 and to also clear connector passage 33 of any residual secretions.

The cross lumen 20 on the plunger 16 of valve 10 applies full suction and airflow to the catheter tip 45 creating this dual low pressure zone 62 action and vortex action 64 within chamber 36. All of this dual cleaning action begins to take place to loosen and remove secretions 59 in the direction of catheter tip 45 even before the instillation of flush fluid through the port 57. The creation and effectiveness of this dual cleaning action is maximized through the use of the high efficiency suction control valve 10.

Figure 9:
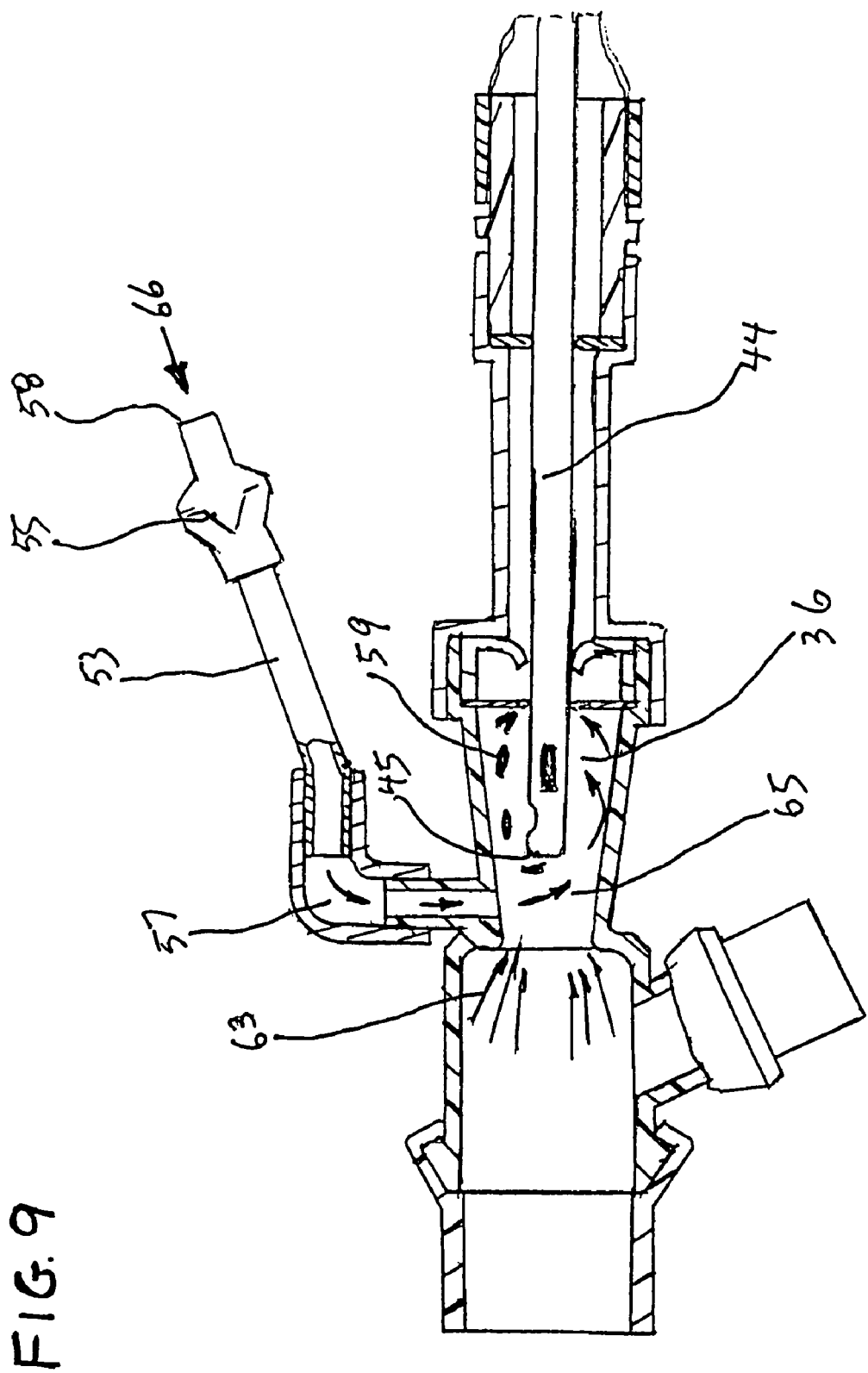
FIG. 9 is a partial side cross-sectional view showing the vortex action of the cleaning chamber when used in conjunction with the installation of catheter rinse fluid.

FIG. 9 depicts the instillation of the catheter flush fluid 66 into housing 54, which opens duckbill valve 55 by unit dose squeeze vial or 20 cc syringe, and instills a swirling rinse liquid air vortex stream 65 in chamber 36 to thoroughly flush and remove secretions 59 as shown. Even the most viscous secretions will be removed within chamber 36 such that essentially no secretions remain which will significantly prevent their reintroduction when the catheter 44 is advanced through chamber 36 upon subsequent suctioning procedures. After catheter cleaning is completed as depicted in FIG. 9, the catheter 44 is fully retracted into isolator tunnel 43 to its original fully 100% isolated position as to shown in FIG. 6 wherein both the catheter 44 and the chamber 36 are thoroughly cleaned. The seal 39 is 100% positively sealed airtight closed upon full withdrawal of catheter 44 such that the passage 33 in connector 30 is completely and hermetically sealed off from catheter 44. By comparison, the Ballard Trach-Care® 72 product, which is the commercial embodiment of Crump et al's U.S. Pat. No. 6,227,200, always leaves the catheter within the front connector air stream since the pivotal flap valve is vented and partially open at all times. This is not the case with the present invention.

Figure 10:
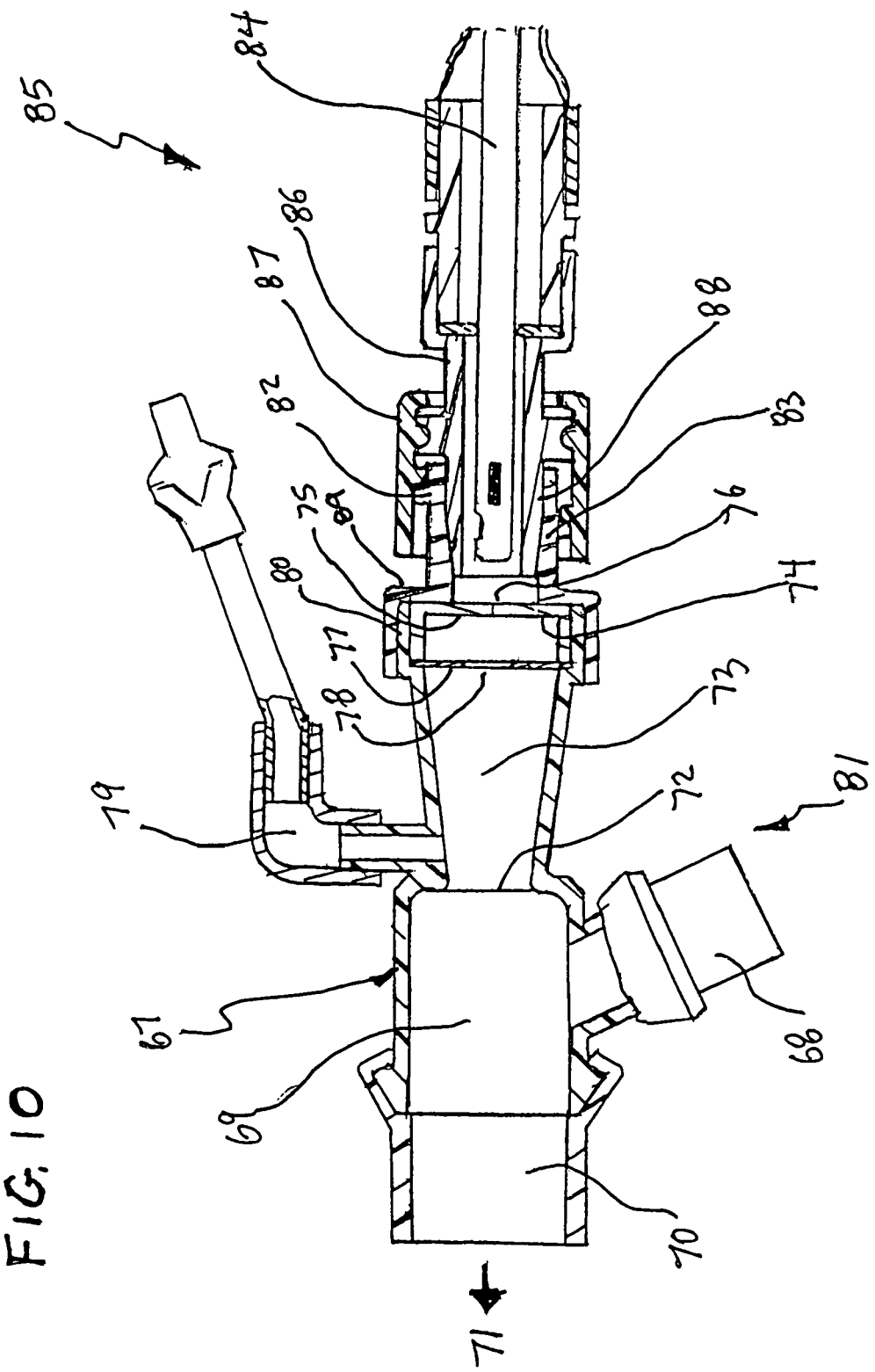
FIG. 10 is a partial side cross-sectional view of an alternate embodiment of the closed tracheal suction system shown in FIG. 6 wherein a replaceable catheter cartridge is shown attached to the frontal connector portion of the system.

FIG. 10 depicts a slightly alternate embodiment having a frontal manifold 67 configured for delivery of ventilator air to a patient through side swivel 68 into interior air passage 69 and out through the front swivel 70 into a patient's respiratory system 71. The air passage 69, side swivel 68 and frontal swivel 70 are located at the distal end of manifold 67. The entrance opening 72 leading into the catheter-cleaning chamber 73 is directly adjacent passage 69. The catheter isolator seal 74 located proximally in the cleaning chamber is molded from silicone rubber and incorporates a thin walled diaphragm 75 with a slit opening 76 centrally located in the diaphragm 75. Disposed between entrance opening 72 and isolator seal 74 is a very thin walled silicone catheter wiper 77 having a central opening 78. Access port 79 permits the delivery of aerosol or liquid fluid into chamber 73 for catheter flushing or the delivery of to lavage or medication. Both the seal 74 and wiper 77 are slightly compression fitted into recess bushing 80 that is solvent cemented into place by a threaded collar 89.

In summary, this assembly forms a first part swivel manifold 81 which when attached to a ventilator circuit on side swivel 68 and to an airway tube on front swivel 70 is 100% positively sealed from outside atmosphere and from the loss of ventilator air to outside atmosphere by the isolator seal 74 that is normally biased to a closed sealed position. The collar 89 has an external quarter turn thread 82 and a tapered opening 83 forming a channel to the isolator seal 74. The elongated suction tube or catheter 84 can open slit 76 solely upon manual contact and insertion of the catheter 84 through slit 76 to suction a patient's airway. Retraction of catheter 84 from slit 76 will automatically return the seal 74 to its normally sealed closed to atmosphere position. The catheter 84 can be configured to be part of a second part catheter cartridge 85 that can form a coupling relationship with the first part swivel manifold 81. The cartridge 85 may include a plastic molded catheter guide channel 86 with rotating quarter turn collar 87 which forms an easy to engage and disengage coupling relationship with the collar 89 such that the taper 88 on the channel 86 forms an airtight tapered lock with tapered opening 83 on collar 89. The catheter 84 is normally positioned within channel 86 ready to be advanced or retracted through seal 74. Since the seal 74 always remains positively sealed to atmosphere, the second part catheter cartridge 85 can be coupled and uncoupled from first part frontal manifold 81 as desired without loss of ventilator air or PEEP to atmosphere. The first part frontal manifold 81 can remain as part of the ventilator circuit while replacement cartridges 85 can be coupled to manifold 81 as desired.

The alternate embodiment described in FIG. 10 has all the clinical advantages of the system depicted in FIG. 6 but instead of being completely unitized as FIG. 6 shows, the system can be a two-part system as shown in FIG. 10 with the catheter-cleaning chamber 73 remaining to be a part of manifold 81. The catheter 84 is easily attached to the high efficiency suction control valve of FIG. 2 such that the cartridge 85 can incorporate all the advantages of the suction control valve 10 in FIG. 2 and become a two-part closed tracheal suction system.

Figure 11:
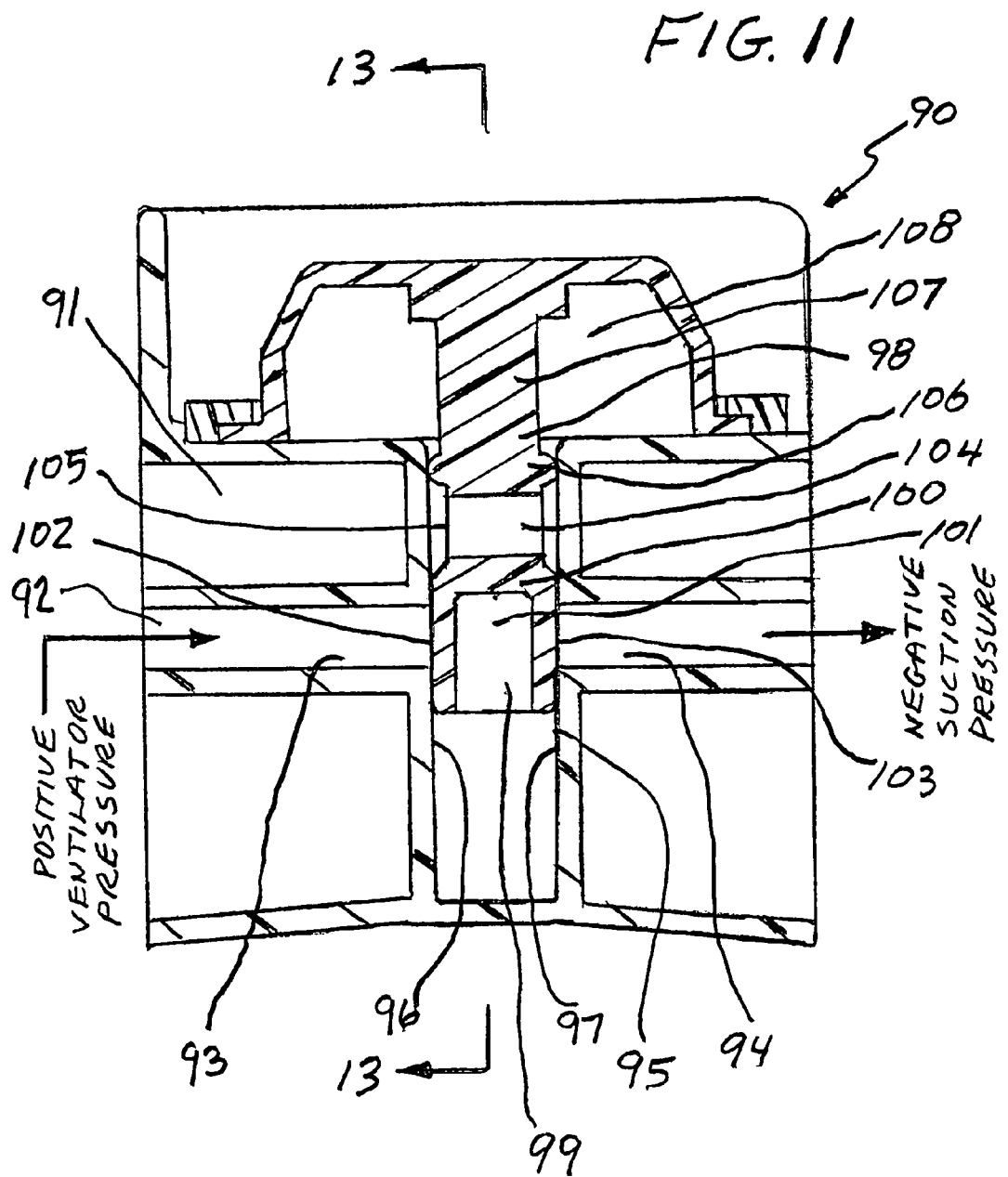
FIG. 11 is an enlarged cross-sectional side view of the high efficiency suction control valve depicting the sealing engagement of the outwardly expanding sidewalls when the valve is in its normally sealed closed non-suction applied position.

FIG. 11 is an enlarged cross-sectional side view more clearly depicting the internal structure of the valve 10 and referred to for purposes of clarity in FIGS. 11-15 as valve 90. The housing 91 of the valve 90 has a main first central linear straight through fluid and airflow passageway 92 comprising a distal passageway 93 subjected to positive ventilator pressure up to 40 mm Hg and the proximal passageway 94 subjected to negative pressure up to 300 mm Hg when the valve is connected to a suction source. Crossing distal passageway 93 and proximal passageway 94 is a second transverse passageway 95 typically circular in cross section and having inner sidewalls 96 and 97. Assembled and inserted into transverse passageway 95 is one-piece synthetic rubber molded resilient plunger 98 constructed from silicone, neoprene or santoprene elastomer with a flexible durometer between 40 and 80 shore A durometer material.

The plunger 98 has a lower piston portion 99 dosed off by internal bridge 100 wherein the piston portion 99 is normally positioned within the second transverse passageway 95 to a non-suction applied position. The piston portion 99 has a hollowed out section 101 having thin, flexible and outwardly expanding sidewalls 102 and 103 dimensioned to only about 0.050 inches in thickness on both sides of hollow section 101.

For comparative purposes, the passageway 95 may be approximately 0.300 inches in diameter and the outer diameter of the piston portion 99 slightly oversized in the order of 0.300 to 0.310 inches. It will be apparent that this oversized interference fit between piston 99 and passageway 95 is possible because of the thin wall structure of the hollowed out section 101 and the flexible nature of the materials from which such is formed. In that regard, the outer wall surfaces of the sidewalls 102 and 103 (actually a continuous outer wall surface) is forced into sealing contact with the inner wall surfaces of the passageway 95 assuring the desired seal therebetween. The smooth operational movement of the piston 99 within the passageway is also assured by the ability of the sidewalls 102 and 103 to flex or vertically bulge inwardly into the hollowed section 101. When the piston is disposed across passageway 92, those portions of the sidewalls 102, 103 previously restrained as above described in the passageway 95 are free to outwardly expand to the extent of the oversized dimensioning between the piston 99 and the passageway 95 above referred to, that is, by 0.010 inches. This outward expansion of the piston walls assures a very tight seal against the adjacent edges of the passageways 93, 94 as desired. Stated differently, hollowed out section 101 permits sidewalls 102 and 103 to expand outward about 0.010 inches against the second transverse passageway sidewalls 96 and 97 to form a 100% positive and negative pressure proof and airtight slideable seal to hermetically seal off fluid and airflow communication between distal passageway 93 and proximal passageway 94. Distal passageway 93 connects to either the suction tube or catheter, and the proximal passageway 94 connects to a source of suction.

The piston portion 99 includes an open unobstructed straight through lumen portion 104 having slightly recessed or chamfered non-sidewall contacting sides 105. Positioned above lumen portion 104 is a built-in slideable molded-in "O" ring wiper seal protrusion 106 that also outwardly expands about 0.010 inches with inner sidewalls 96 and 97 to completely seal of the upper plunger to portion 107 and internal actuator portion 108 to prevent any suctioned secretions or fluid from entering in these areas that could breed bacteria and viruses which could re-infect the patient.

In essence, the wiper seal 106 serves a unique dual purpose to both wipe down fluid or secretions into the lumen portion 104 and to seal off fluid access into the upper plunger portion 107 during depressible and releasable operation of the plunger 98 in the second transverse passageway 95.

Figure 12:
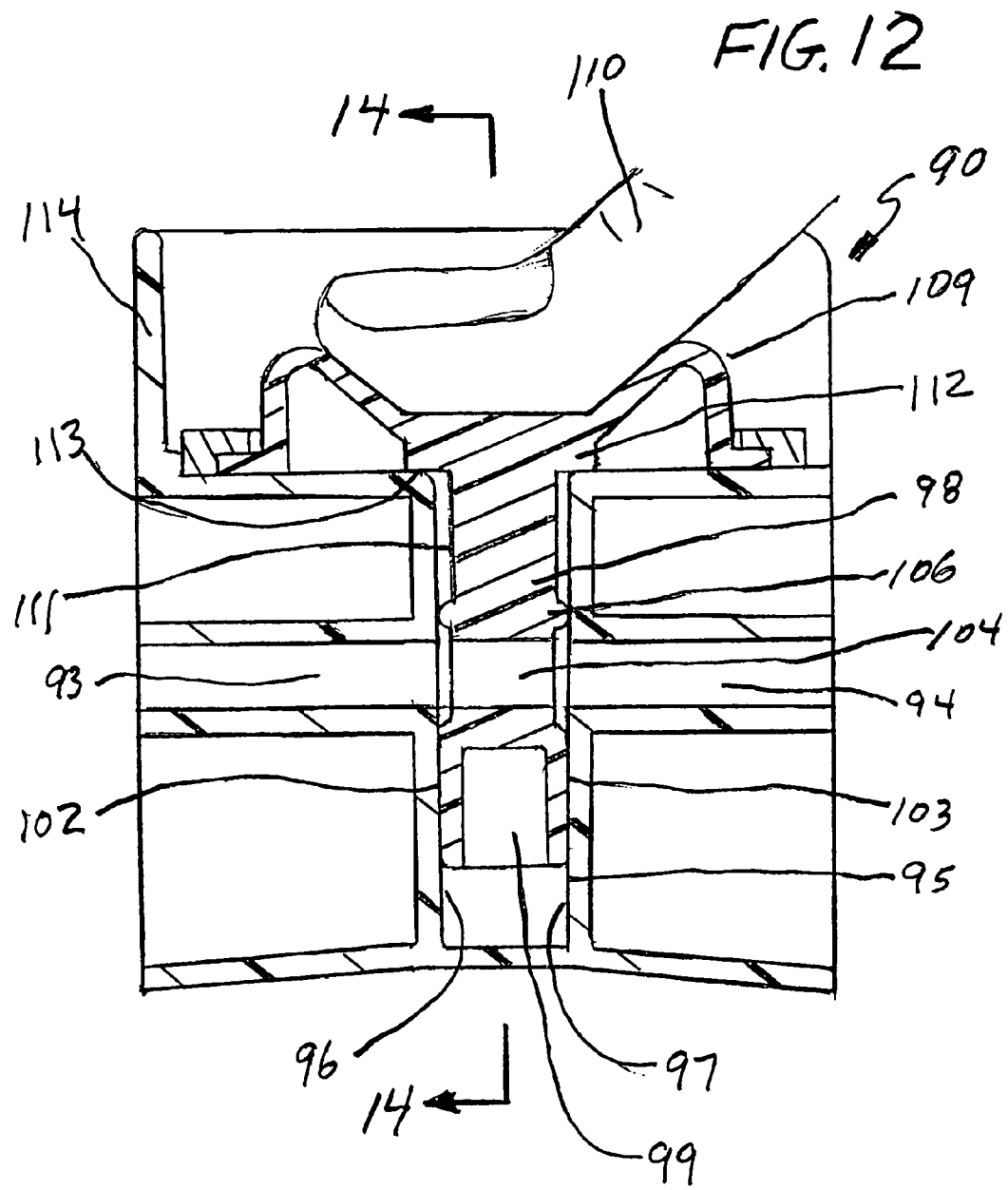
FIG. 12 is an enlarged cross-sectional side view of the high efficiency suction control valve depicting the depression stop part of the actuator portion of the plunger when the valve is actuated to its fully opened suction applied position.

FIG. 12 is also an enlarged cross-sectional side view of the valve 90 except depicted in its actuator 109 depressed suction applied position. As noted, both the actuator 109 and plunger 98 along with their respective elements are preferably molded in one-piece configuration from resilient synthetic rubber.

Both the wiper seal 106 and the piston portion 99 sidewalls 102 and 103 form a slightly outwardly expanding sealing engagement with the sidewalls 96 and 97 portions of the second passageway 95 thus ensuring a 100% positive and negative pressure proof and airtight slideable seal. Stated differently, the lower or piston portion of the plunger forms a first slideable seal and the upper or wiper seal portion of the plunger forms a second slideable seal, which first and second slideable seals co-act to maintain PEEP at all times during operation of the system. Also since the only portions forming a slideable sealing engagement with the second transverse passageway 95 are the wiper seal 106 and the lower piston portion 99, the thumb 110 depressive force and any excessive drag caused by the plunger 98 within second passageway 95 is minimized. Also as the plunger is depressed, gas (air) in the closed system is to some extent compressed in the hollowed out portion 101. This also provides instant return action of the plunger 98 to its original non-suction applied position depicted in FIG. 11.

The slightly recessed upper sidewall contacting sides 111 on plunger 98 further minimizes drag and provides instantaneous return action of the actuator 109 upon manual release of the depressible actuator 109. The wiper seal 106 further acts as a wiper seal to wipe down any secretions that may accumulate on inner sidewalls 96 and 97 into the lumen portion 104 and out through proximal suction passageway 94 and to seal off actuator 108 from fluid. In this manner, the both the upper wiper seal 106 and lower piston portion 99 form a combination of elements to selectively engage the second transverse passageway 95 to provide an excellent slideable seal with minimal drag for rapid and instantaneous return action of the actuator 109.

Rapid return action of the actuator 109 is critical since suction is only applied for a short time period (typically no more than 15 seconds) to reduce oxygen depletion within the airway and while the actuator is repeatedly and intermittently depressed to avoid constant suction from being applied to delicate mucosal tissue from the suction tube distal tip.

The plunger 98 therefore creates a slideable seal both above and below the lumen portion 104. The seal is formed by the upper wiper seal 106 and lower piston portion 99 both having outwardly expanding sidewalls forming direct sealing engagements with different portions of the inner sidewalls 96 and 97 within second transverse passageway 95. The actuator 109 has a built-in depression stop 112, which is a circular flat ledge, that will positively come to rest on top of the flat surface 112 portion of the rigid injection molded housing 114.

When the actuator 109 is fully depressed to its suction applied position as shown in FIG. 12, depressive stop 112 insures that the lumen portion 104 is perfectly aligned with distal passageway 93 and the proximal passageway 94 for maximum suction efficiency and unobstructed fluid flow.

Figure 13:
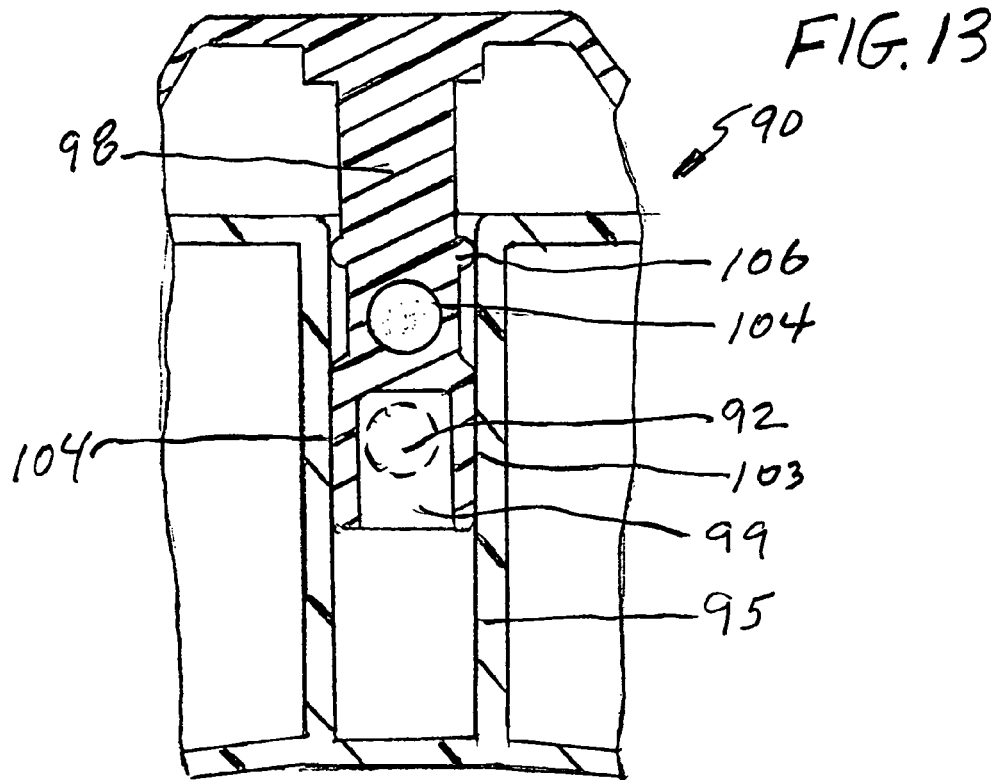
FIG. 13 is a partial cross-sectional end view of the high efficiency suction control valve depicting the sealing engagement of the outwardly expanding sidewalls when the valve is in its normally sealed closed non-suction applied position taken along lines 13-13 from FIG. 11.

FIG. 13 is a partial cross-sectional end view of the valve 90 taken along lines 13-13 from FIG. 12 wherein the valve 90 is depicted in its non-suction applied position. The upper wiper seal 106 is shown above the lumen portion 104, and the lower piston portion 99 is shown below the lumen portion 104. As can be seen, the lower piston portion 99 with its outwardly expanding sidewalls 103 and 104 hermetically seal off central linear fluid and airflow passageway 92.

Figure 14:
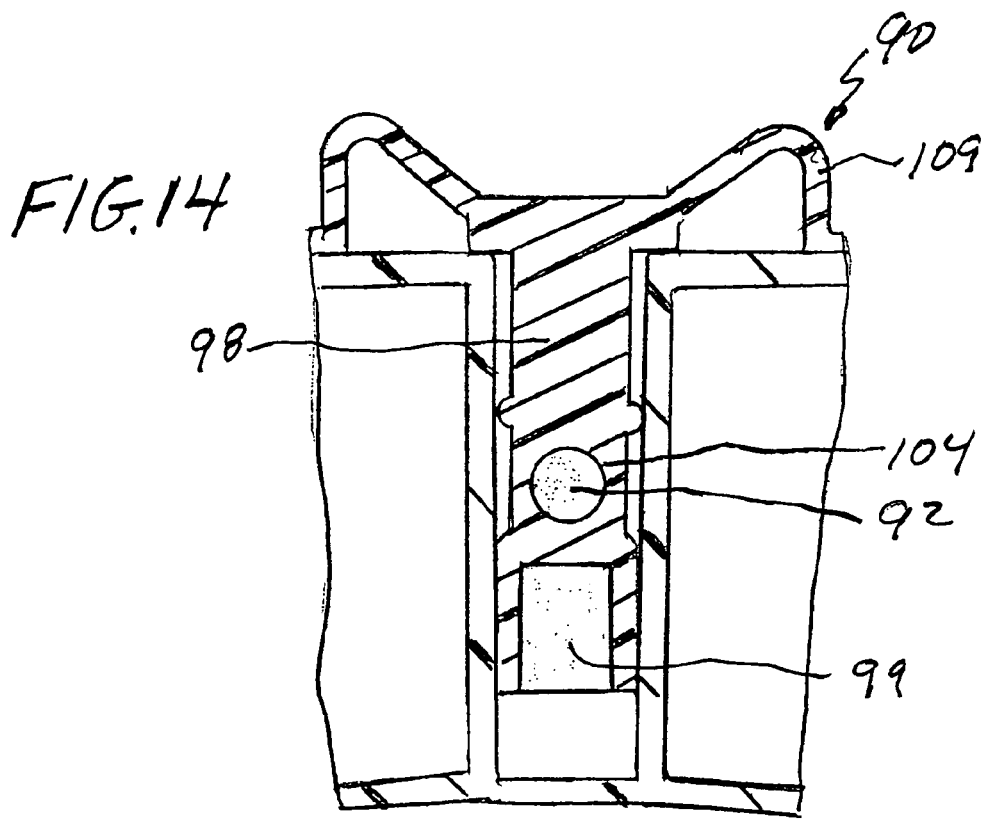
FIG. 14 is a partial cross-sectional end view of the high efficiency suction control valve depicting the depression stop part of the actuator portion of the plunger when the valve is actuated to its fully opened suction applied position taken along lines 14-14 from FIG. 12.

FIG. 14 is a partial cross-sectional end view of the valve 90 taken along lines 14-14 from FIG. 13 wherein the valve 90 is depicted in its suction applied position. The cross lumen portion 104 on the plunger 98 is now perfectly aligned with passageway 92 to form an unobstructed straight through secretion removal passageway.

FIG. 15 is a cross-sectional side view of valve 115 similar in many respects to valve 90 depicted in FIG. 11 with the exception of a slightly differently designed plunger 116 wherein the lower piston portion 117 incorporates cross lumen 118 and has outwardly expanding sidewalls 119 below cross lumen 118 and an oversized and thus continually compressed, i.e., an outwardly expanding, wiper seal 120 directly above cross lumen 118 to seal off actuator 123. In this design, the lower piston portion 117 incorporates both elements of the wiper seal 120 and an unobstructed straight through lumen 118. In this configuration, the walls defining the cross lumen 118 also are oversized with respect to the second passageway 95 and thus, so to speak, has an outwardly expanding sidewall 121 such that the entire lower piston portion 117 acts as an outwardly expanding slideable seal. Drag is also kept to a minimum since the plunger 116 has a recess 122 and thus non-contacting upper sidewalls located above wiper seal 120.

This alternate embodiment as depicted in FIG. 15 has all the advantages of the embodiment shown in FIG. 12 with the addition that the cross lumen also has a slideable sealing surface.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A suction system having a suction tube, a source of suction, and a suction control valve, said suction control valve comprising a housing having a first central circular passageway extending through and thus creating an air and fluid flow path area through said housing and in fluid communication at one end thereof with the suction tube and with the suction source at the other end thereof, said housing having a second circular passageway which traverses said first central passageway and terminates in an airtight lower terminal portion defined by said housing, a resiliently molded manually movable and releasable plunger operable in connection with said second passageway wherein said plunger includes an upper portion and a lower portion, said lower portion having a first slideable seal to seal said first central passageway and said upper portion having a second slideable seal positioned above said first slideable seal, said second slideable seal having straight sided sidewalls including an outwardly expanding completely circular wiper seal protrusion compressively form fitted into said second passageway, said lower portion being normally positioned with said plunger in a normally downwardly resiliently compression biased non-suction applied position and further manually movable to a suction applied position said plunger having a cross lumen of a cross-sectional area at least as large as the cross-sectional area of said first passageway such that when the cross-sectional area of said cross lumen is aligned with the cross-sectional area of said first passageway, said cross lumen does not restrict the flow path area of said first passageway so as to create an unrestricted and unobstructed negative pressure air flow path and unrestricted and unobstructed fluid secretion flow path communication between said suction tube and said source of suction, and said second slideable seal preventing fluid access to said upper portion of the plunger during the manual movement of said plunger to said suction applied position.

2. The suction system claim 1 wherein the suction tube is a suction catheter.

3. The suction system of claim 1 wherein the system is a closed tracheal suction system.

4. The suction system of claim 1 wherein the system is attached to a ventilator.

5. The suction system of claim 1 wherein the plunger is molded in one piece.

6. The suction system of claim 1 wherein the plunger includes an actuator.

7. The suction control valve of claim 1 wherein the valve includes a means for preventing inadvertent depression of the plunger.

8. The suction system of claim 1 wherein said plunger automatically returns to its non-suction applied position upon manual release of said plunger.

9. The suction system of claim 1 wherein said first slideable seal includes a piston portion normally sealing off said first passageway to a non-suction applied position.

10. The suction system of claim 9 wherein said second slideable seal includes outwardly expanding flexible side walls defining an O-ring wiper seal.

11. A suction system having a suction tube, a source of suction and a suction control valve, said suction control valve comprising: a housing having a first central passageway extending through said housing and in fluid communication at one end thereof with the suction tube and with the suction source at the other end thereof, said housing having a second passageway which traverses said first central passageway, a resiliently molded manually activated and releasable plunger normally downwardly resiliently compression biased within said second passageway wherein said plunger includes an upper portion and lower portion, said lower portion providing an open, unobstructed, unrestricted fluid flow path and a dual purpose wiper seal positioned above said fluid flow path, said dual purpose wiper seal having straight sided sidewalls including an outwardly expanding wiper seal protrusion resiliently compressed into said second passageway, said dual purpose wiper seal further serving to both wipe down fluid into said fluid flow path and to seal off fluid access into said upper portion during operation of the plunger within said second passageway.

12. The suction system of claim 11 wherein the suction tube is a catheter.

13. The suction system of claim 11 wherein the system is a closed tracheal suction system.

14. The suction system of claim 11 wherein the system is attached to a ventilator.

15. The suction system of claim 11 wherein the plunger is molded in one piece.

16. The suction system of claim 11 wherein the plunger includes an actuator.

17. The suction system of claim 11 wherein said plunger automatically returns to its non-suction applied position upon manual release of said plunger.

18. The suction system of claim 11 wherein said plunger lower portion includes a closed off piston portion normally positioned to seal off said second passageway when said piston portion is normally downwardly resiliently compression biased to a non-suction applied position, said plunger piston lower portion having walls slightly oversized as compared to the second passageway such that the plunger piston is compressed by said second passageway walls when positioned in the first non-suction applied position.

19. The suction system of claim 18 wherein said lower piston portion includes outwardly expanding flexible side walls on either side of said piston portion to hermetically seal off said second passageway.

20. A suction system having a suction tube, a source of suction, and a suction control valve, said suction control valve comprising: a housing having a first central passageway extending through said housing and in fluid communication at one end thereof with the suction tube and with the suction source at the other end thereof, said housing having a second passageway which traverses said first central passageway, a resiliently molded manually activated and releasable plunger normally downwardly resiliently compression biased within said second passageway wherein said plunger includes an upper portion and a lower portion, said lower portion providing an open, unobstructed and unrestricted flow path in fluid communication with said first central passageway during manual activation of said plunger, said upper portion including a wiper seal positioned above said flow path to prevent fluid access into said upper portion during operation of the plunger within said second passageway, said upper portion of said plunger having straight sided sidewalls including an outwardly expanding oversized protrusion resiliently compressed into said second passageway so as to form said wiper seal.

21. The suction system of claim 20 wherein the suction tube is a suction catheter.

22. The suction system of claim 20 wherein the system is a closed tracheal suction system.

23. The suction system of claim 20 wherein the system is attached to a ventilator.

24. The suction system of claim 20 wherein the plunger is molded in one piece.

25. The suction system of claim 20 wherein the plunger includes an actuator.

26. The suction control valve of claim 20 wherein the valve includes a means for preventing inadvertent depression of the plunger.

27. The suction system of claim 20 wherein said plunger automatically returns to a non-suction applied position upon manual release of said plunger.

28. The suction system of claim 20 wherein said plunger lower portion includes a closed off piston portion normally positioned to seal off said second passageway to a non-suction applied position.

29. The suction system of claim 28 wherein said piston portion includes outwardly expanding flexible side walls on either side of said portion to hermetically seal off said second passageway.

30. A closed suction system adapted to be attached a ventilator constantly delivering positive pressure air into a patient's airway having a suction tube, a source of suction and a suction control valve, said suction control valve comprising: a rigid molded housing having a first central passageway extending through said housing and in fluid flow communications at one end thereof with the suction tube and with the suction source at the other end thereof, said housing having a second passageway which traverses said first central passageway, said second passageway including rigid molded inner surfaces, a resiliently molded manually activated and releasable plunger operable within said second passageway wherein said plunger includes a piston portion, said piston being resiliently flexibly molded so as to form a compressively biased sealing engagement with the rigid inner surfaces of said second passageway, said piston including a wiper seal protrusion and being normally positioned within said second passageway to a normally downwardly resiliently compression biased non-suction applied position where said piston portion is positioned to seal off said first passageway to prevent any loss of positive pressure air leakage past the piston to atmosphere, so as to form a 100% positive air pressure proof and airtight slideable seal to hermetically seal off fluid and positive pressure airflow communication between said suction tube and atmosphere, said plunger further manually activated within said second passageway to a suction applied position wherein there is unobstructed fluid and airflow communication between said suction tube and said source of suction said plunger automatically returnable to its non-suction applied 100% positive air pressure proof and airtight slideable sealed off position upon manual release of said plunger.

31. The suction valve of claim 30 wherein said piston forms a flexible resilient slideable seal with said rigid inner surfaces, said rigid inner passageway surfaces being formed with a complete 360 degree circular surface contact area with said flexible resilient slideable seal.

32. The suction control valve of claim 30 wherein the valve includes a means for preventing inadvertent depression of the plunger.

33. The suction control valve of claim 30 wherein said plunger includes a high flow air and fluid path which permits unrestricted and unobstructed fluid flow communication between said suction tube and said source of suction when said plunger is manually activated.

34. The suction control valve of claim 33 wherein the valve includes a means for preventing inadvertent depression of the plunger.

35. The suction catheter system of claim 30 wherein the system is a closed tracheal suction system.

36. A closed respiratory suction catheter system for suctioning secretions from a patient comprising: a frontal manifold configured for delivery of positive pressure ventilator air to a patient, a rearward suction control valve adapted for attachment to a source of suction, a suction catheter assembly including a suction catheter disposed between and operatively connecting the frontal manifold and the rearward suction control valve, said suction control valve in fluid and airflow communication at one end thereof with the suction catheter and at its other end with the source of suction, said suction control valve comprising: a housing having a first central passageway extending through said housing and in fluid flow communications at one end thereof with the suction catheter and with a suction source at the other end thereof, said housing having a second passageway opening which traverses said first central passageway, a manually activated and releasable plunger operable within said second passageway wherein said plunger includes a closed piston portion and an unrestricted and unobstructed open flow path portion, said piston including a downwardly biased slideable seal forming an interference fit sealing engagement with said second passageway, said piston including a wiper seal protrusion and being normally positioned within said second passageway to a normally downwardly resiliently compression biased non-suction applied position where said piston portion is positioned to seal said first passageway to prevent any loss of positive pressure air leakage out the piston to atmosphere so as to form a 100% positive air pressure proof and airtight slideable seal to hermetically seal off fluid and airflow communication between said suction tube and said source of suction, said plunger further manually operable and activated within said second passageway to a suction applied position wherein there is unrestricted and unobstructed fluid and airflow path communication between said suction tube and said source of suction, said plunger automatically returnable to its non-suction applied 100% positive air pressure proof and airtight slideable sealed off position upon manual release of said plunger.

37. The respiratory suction system of claim 36 wherein said piston is downwardly compression biased by an actuator to its normally biased non-suction applied position.

38. The respiratory suction system of claim 36 including a means for cleaning the catheter.

39. The respiratory suction system of claim 36 wherein the frontal manifold is fixedly connected to a suction catheter assembly.

40. The respiratory suction system of claim 36 wherein the suction catheter assembly is disconnectable with the frontal manifold.

41. A closed respiratory suction catheter system for suctioning secretions from a patient comprising: a frontal manifold configured for delivery and maintenance of positive pressure ventilator air to a patient, a rearward combination positive pressure and negative pressure control valve adapted for attachment to a source of suction, a suction catheter assembly including a suction catheter disposed between and operatively connecting the frontal manifold to the rearward combination positive pressure and negative pressure control valve, said combination positive pressure and negative pressure control have having opposed ends with one end thereof in positive pressure airflow and fluid secretion communication with the suction catheter and connected at its other end with the suction source, said combination positive pressure and negative pressure control valve comprising a rigid housing having a rigid inner passageway, a manually operable resilient plunger slideably operable within the passageway, said plunger compressibly fitted within the rigid inner passageway and forming an airtight slideable seal, said plunger including a wiper seal protrusion and being normally biased to a non-suction applied position wherein said slideable seal forms a positive pressure airtight hermetic 360 degree completely circular compression biased surface fit within the passageway wherein the passageway has a mating 360 degree completely circular surface fit with the slideable seal to prevent any loss of positive pressure ventilator air from the catheter and out to atmosphere thereby maintaining positive pressure ventilator air within the frontal manifold, said plunger further manually slideably operable to a suction applied position within the passageway wherein the slideable seal further prevents any fluid secretion leakage past the slideable seal and there is unrestricted and unobstructed negative pressure airflow and unrestricted and unobstructed fluid secretion flow path communication between said catheter and said suction source, and said plunger slideably and automatically returnable to its non-suction applied airtight hermetically sealed position upon manual release of said plunger.

42. The control valve of claim 41 wherein the resilient slideable seal is slideably operable by a downwardly biasing actuator.

43. A closed respiratory suction catheter system for suctioning secretions from a patient comprising: a frontal manifold configured for delivery and maintenance of positive pressure ventilator air to a patient, a rearward combination positive pressure and negative pressure control valve adapted for attachment to a source of suction, a suction catheter assembly including a suction catheter disposed between and operatively connecting the frontal manifold to the rearward combination positive pressure and negative pressure control valve, said combination positive pressure and negative pressure control valve having opposed ends with one end thereof in positive pressure airflow and fluid secretion communication with the suction catheter and connected at its other end with the suction source, said combination positive pressure and negative pressure control valve comprising: a manually operable resilient plunger slideable seal positioned within a passageway within the control valve, the plunger slideable seal including a wiper seal protrusion and being normally downwardly resiliently compression biased to a non-suction applied position to prevent both loss of ventilator positive pressure air leakage and fluid secretion leakage from the catheter out to atmosphere wherein said plunger slideable seal having a flexible resiliently molded sealing piston fitted within the passageway forming an airtight downwardly biased compressive hermetic seal with said passageway, said plunger slideable seal further manually operable to a suction applied position wherein there is unrestricted and unobstructed negative pressure airflow and unrestricted and unobstructed fluid secretion flow path communication between said catheter and said source of suction, and said plunger slideable seal automatically returnable to its normally downwardly resiliently compressively biased non-suction applied airtight hermetic seal position upon manual release of said plunger slideable seal.

44. The suction system of claim 43 wherein the system is a closed tracheal suction system.

45. The suction system of claim 43 wherein the system is attached to a ventilator.

46. The suction system of claim 43 wherein the resilient plunger is a one-piece molded component.

47. The suction system of claim 43 including a means for instillation of flushing fluid to clean the catheter.

48. The suction system of claim 43 wherein the plunger is manually slideably operated by an actuator forming a 360 degree completely circular surface to circular surface airtight hermetic seal between said plunger and said passageway.

49. The combination valve of claim 43 wherein the valve includes a means for preventing inadvertent actuation of the plunger slideable seal.

50. A closed respiratory suction catheter system for suctioning secretions from a patient comprising: a frontal manifold configured for delivery and maintenance of positive pressure ventilator air to a patient, a rearward combination positive pressure and negative pressure control valve adapted for attachment to a source of suction, a suction catheter assembly including a suction catheter disposed between and operatively connecting the frontal manifold and the rearward combination positive pressure and negative pressure control valve, said combination positive pressure and negative pressure control valve having opposed ends with one end thereof in positive pressure airflow and fluid secretion communication with the suction catheter and connected at its other end with the suction source, said combination positive pressure and negative pressure control valve comprising: a rigid housing having an inner passageway, a manually operable molded plunger with sidewalls having a built-in resilient flexible molded slideable wiper seal protrusion positioned and compressively biased within the passageway, said plunger normally slideably biased to a non-suction applied position wherein said built-in resilient flexible molded slideable seal serves the dual purpose of wiping down any fluid secretions within the passageway as well as acting as a positive pressure airtight hermetic 360 degree completely circular compression biased seal within the passageway wherein the passageway has a mating 360 degree completely circular surface sealing fit with the slideable seal to prevent any loss of positive pressure ventilator air from the catheter and out to atmosphere thereby maintaining positive pressure ventilator air within the frontal manifold, said plunger further slideably manually operable to a suction applied position wherein there is unrestricted and unobstructed negative pressure airflow and unrestricted and unobstructed fluid secretion flow path communication between said catheter and said source of suction, and said plunger automatically returnable to its non-suction applied airtight hermetic seal position upon manual release of said plunger.

51. The control valve of claim 50 wherein the wiper seal protrusion includes an O-ring which is downwardly compressively biased within the passageway.

52. The control valve of claim 50 wherein the resilient plunger and the slideable seal are an integrally molded component.

53. The control valve of claim 50 wherein the plunger is manually slideably operated by a downwardly biasing actuator.

54. The control valve of claim 50 wherein the valve includes a means for preventing inadvertent slideable actuation of the plunger.

55. The suction system of claim 50 including a means for installation of flushing fluid to clean the catheter.

56. The suction system of claim 50 including at least one wiper to clean the catheter.

57. The suction system of claim 50 including a sleeved catheter.

58. The suction system of claim 50 wherein the catheter is advanceable and retractable through the frontal manifold.

* * * * *